United States Patent [19]
Rosenquist

[11] Patent Number: 5,962,558
[45] Date of Patent: Oct. 5, 1999

[54] HIGH MOLECULAR WEIGHT STABILIZER COMPOUNDS FOR STABILIZING POLYMERS

[75] Inventor: Niles R. Rosenquist, Vanderburgh, Ind.

[73] Assignee: General Electric Company, Pittsfield, Mass.

[21] Appl. No.: 09/105,642

[22] Filed: Jun. 26, 1998

Related U.S. Application Data

[62] Division of application No. 08/631,592, Apr. 12, 1996, Pat. No. 5,807,963, which is a division of application No. 08/361,264, Dec. 21, 1994, Pat. No. 5,523,379.

[51] Int. Cl.[6] .................................................. C08K 5/34
[52] U.S. Cl. ............................................................ 524/91
[58] Field of Search .................................................. 524/91

[56] References Cited

U.S. PATENT DOCUMENTS

| | | | |
|---|---|---|---|
| 3,303,331 | 2/1967 | Biegel et al. | 235/470 |
| 3,419,634 | 12/1968 | Vaughn, Jr. | 528/29 |
| 3,635,895 | 1/1972 | Kramer | 525/462 |
| 3,697,481 | 10/1972 | Bialous et al. | 528/196 |
| 3,832,419 | 8/1974 | Merritt, Jr. | 528/21 |
| 4,001,184 | 1/1977 | Scott | 528/182 |
| 4,128,559 | 12/1978 | Pond et al. | 548/261 |
| 4,153,780 | 5/1979 | Narita et al. | 528/198 |
| 4,159,069 | 6/1979 | Poncy et al. | 223/111 |
| 4,188,314 | 2/1980 | Fox et al. | 524/494 |
| 4,194,038 | 3/1980 | Baker et al. | 528/182 |
| 4,535,104 | 8/1985 | Pyles | 524/91 |
| 4,681,922 | 7/1987 | Schmidt et al. | 525/474 |
| 4,762,896 | 8/1988 | Fox et al. | 525/462 |
| 4,782,103 | 11/1988 | Ogoe | 524/83 |
| 4,814,395 | 3/1989 | Rosenquist | 525/433 |
| 4,826,928 | 5/1989 | Rosenquist | 525/439 |
| 4,853,471 | 8/1989 | Rody et al. | 548/261 |
| 4,923,933 | 5/1990 | Curry | 525/439 |
| 4,960,839 | 10/1990 | Rosenquist | 55/462 |
| 4,973,702 | 11/1990 | Rody et al. | 548/261 |
| 4,999,408 | 3/1991 | Rosenquist | 525/463 |
| 5,025,081 | 6/1991 | Fontana et al. | 528/176 |
| 5,032,498 | 7/1991 | Rody et al. | 430/512 |
| 5,081,205 | 1/1992 | Rosenquist | 525/462 |
| 5,412,059 | 5/1995 | Connell et al. | 528/183 |

FOREIGN PATENT DOCUMENTS

| | | |
|---|---|---|
| 0 272 422 A2 | 6/1988 | European Pat. Off. . |
| 0 417 514 A2 | 3/1991 | European Pat. Off. . |
| 0 494 601 A2 | 7/1992 | European Pat. Off. . |
| 0 682 082 A2 | 11/1995 | European Pat. Off. . |
| 0 683 192 A2 | 11/1995 | European Pat. Off. . |

*Primary Examiner*—Kriellion A. Sanders

[57] ABSTRACT

A high molecular weight stabilizer compound formed as an ester of 3-(2H-benzotriazol-2-yl)-5-(1,1-dimethylethyl)-4-hydroxy-benzene-propanoic acid, or structural variants thereof, to impart improved resistance to the effects of ultraviolet radiation to polycarbonate comprising polymers, a process for the preparation of said compound, and articles of manufacture comprising said compound.

10 Claims, No Drawings

HIGH MOLECULAR WEIGHT STABILIZER COMPOUNDS FOR STABILIZING POLYMERS

This is a divisional of application Ser. No. 08/631,592 filed on Apr. 12, 1996 now U.S. Pat. No. 5,807,963, which is a divisional of Ser. No. 08/361,264 filed on Dec. 21, 1994, which is now issued U.S. Pat. No. 5,523,379.

FIELD OF THE INVENTION

The present invention relates to a composition having a high molecular weight useful either singly or in combination as a stabilizer for various polymeric materials. More particularly, the present invention relates to a polycarbonate, copolyestercarbonate, or polysiloxane copolycarbonate wherein the chain terminating functional groups act to impart a stabilizing function to the polymer molecule. More particularly, the stabilizing function imparted to the polymer molecule is an improved resistance to the deleterious effects of ultraviolet radiation.

The present invention also provides a method of preparing the composition of the invention. Further the present invention also provides for articles of manufacture comprising the composition of the present invention.

BACKGROUND OF THE INVENTION

Polycarbonates, copolyestercarbonates, and polysiloxane copolycarbonates are high polymers produced by the condensation or intercondensation of a dihydroxy compound and a diacid or reactive derivative thereof such as an acid halide. When the dihydroxy compound is bisphenol-A and the acid derivative is phosgene, a simple polycarbonate (PC) polymer results. Similarly terephthalic acid and ethylene glycol intercondense to form polyethylene terephthalate (PET). Since these polymers are polyesters of bifunctional precursor monomers, it is theoretically possible for the reaction mixture to go entirely to completion and create one entire reaction vessel filling molecule. In practice, of course, this does not occur because as the polymerization increases the average chain length of the polymer increases, the viscosity of the reaction medium increases and the reaction probability decreases because there are progressively fewer complementary reactive species in a unit volume of the reaction vessel. Thus the reaction slows and eventually terminates on the basis of the statistics of reaction probability and the statistics of the polymer chain conformation because a reactive acid-derived terminus is statistically unlikely to find and react with a reactive hydroxyl terminus.

In producing these types of polyester polymers, endcapping or chain terminating agents are employed. In order to effectively terminate the growing end of a polymer molecule, these chain terminating or endcapping species must be monofunctional such that when reaction occurs with the growing end of the polymer molecule, further growth in the chain length of the particular polymer molecule is terminated. Thus depending on the statistical mechanics of polymer growth, there should be at least a rough correlation between the quantity of chain terminating agent, on a molar basis, and the average molecular weight of the polymer. Indeed, one function of endcapping agents, aside from the elimination of reactive ends, is to regulate the average molecular weight of the polymer being synthesized.

Typical endcapping agents have been monofunctional compounds of low molecular weight, high reactivity, readily available and cheap. Additionally such compounds have been monofunctional analogs of one or the other bifunctional monomers being polymerized. Thus in the case of polycarbonates, typical endcapping agents are various phenols such as phenol, tertiary-butyl-phenol, and para-cumylphenol. Other endcapping agents have been disclosed such as chromanyl in U.S. Pat. No. 3,697,481 to Bialous et al. herewith incorporated by reference. In general, aromatic polycarbonates and polycarbonate copolymers may be produced by various methods such as shown in U.S. Pat. Nos. 3,635,895 and 4,001,184, herewith incorporated by reference.

Variations in the mole ratio between the chain terminating compounds, such as phenol, and the chain growing compounds, such as bisphenol-A and phosgene, lead to the ability to control the molecular weight of the resulting polymer. Higher levels of chain terminating agents in the reaction mixture tend to lead to lower average molecular weights or shorter average polymer chain length. Conversely, lower levels of chain terminating agents in the reaction mixture tend to lead to higher average molecular weights or longer average chain length.

Frequently there are additional considerations or advantages associated with the choice of a particular chain terminating agent. Being esters, polymers such as polyesters, copolyestercarbonates, polycarbonates, polysiloxane copolycarbonates and the like are susceptible to hydrolysis and trans-esterification. A chain terminating agent that reduces the susceptibility of these polymers to hydrolysis or trans-esterification can impart improved properties to the polymer as well as functioning as a polymer chain length regulator during synthesis.

When put to use, these polymers may be alloyed with other polymers and/or compounded with various stabilizing and functionalizing additives. The additive compounds or mixtures of additive compounds are typically incorporated to prohibit undesired reactions of the polymer to the physical or chemical challenges experienced either during the process of converting the polymer to a useful article of manufacture or during the useful life of the manufactured article containing the stabilized polymer. These physical and chemical challenges include among others, slow oxidation, rapid oxidation (combustion), photolytic degradation, thermal degradation, and hydrolytic degradation. Consequently, depending on a particular polymer, there are to be found various stabilizer compounds available commercially either singly or in combination that improve or render more stable one or more of the physical or chemical properties of the polymer.

A particular problem associated with the polycarbonate family of polymers is stability to photolytic degradation, especially that caused by ultraviolet radiation. There are accordingly a large variety of stabilizer compounds useful to impart an improved resistance to the effects of ultraviolet radiation upon polycarbonate polymers. Among these stabilizer compounds are the phenolically substituted benzotriazole compounds. At low levels of addition to the polymer formulation, below about 0.5 to about 1.0 weight percent, the benzotriazole ultraviolet stabilizers generally disperse or dissolve in the polymer matrix in a satisfactory fashion and generally impart the desired ultraviolet resistance to the polymer. At higher levels, above about 2 to about 3 weight percent, the benzotriazole stabilizers have a tendency to undergo migration, phase separation, and plate out. This is a significant problem for certain extruded, laminated or layered sheet formulations where the function of the sheet is to provide a protective function for structural or glazing sheet thereunder, because when the stabilizer compound undergoes a phase separation the effective quantity of stabilizer compound present in the polymer matrix is reduced. Additionally, the stabilizer that migrates form the polymer matrix coats and/or plugs the manufacturing process equipment, causing surface defects and other quality problems in the articles being manufactured. This results in increased downtime of the manufacturing equipment for cleaning.

A previous approach exemplified by the teachings of U.S. Pat. No. 4,153,780 (the '780 patent) where phenolically substituted benzotriazoles, active for imparting ultraviolet resistance to polymers, are chemically bound as an endcapping agent to the polycarbonate polymer through the phenolic hydroxyl moiety. This approach incorporates the phenolically substituted benzotriazole as a chain stopping agent into the polymeric molecule. However, by the formation of a covalent chemical bond between the phenolic oxygen of the substituted benzotriazole and the terminal chloroformate group of the growing polycarbonate polymer, the ability of the phenolically substituted benzotriazole to function as an ultraviolet stabilizer is greatly reduced or altogether destroyed. Apparently, the phenol hydroxyl group of the phenolically substituted benzotriazole must be capable of forming a hydrogen bond in order for the molecule to function as an inhibitor for the degradative effects of ultraviolet radiation. While Applicant subscribes to this view as a matter of information and belief as however, the operability of Applicant's invention does not depend on this particular theoretical mechanism. While the incorporation of the benzotriazoles as taught in the '780 patent may render polycarbonates somewhat more stable to ultraviolet radiation, on a comparative basis the addition of an equivalent amount of free, as opposed to polymer bound, benzotriazole stabilizer compound to polycarbonates generally produces a better stabilizing effect in the polymers being treated therewith. Consequently, the benefit that might be achievable by chemical incorporation of the stabilizer molecule into the polymer is more than offset by a loss in efficacy caused by the changes in chemical bonding forced upon the stabilizer molecule when the stabilizer molecule is incorporated into the polymer.

Typically the stabilizer compounds are of a significantly lower molecular weight by comparison to the polymer being stabilized. This large difference in molecular weight leads to problems that are generally categorized as compatibility problems, i.e. the stabilizer may not be soluble in the polymer or because of its low molecular weight, the stabilizer has a tendency to volatilize or migrate out of the polymer matrix. A stabilizer that will not dissolve or disperse in the polymer to be stabilized does not impart any useful benefit to the polymer. Likewise a stabilizer that volatilizes or migrates out of the polymer matrix also does not impart any useful benefits to the polymer, and causes problems during manufacturing. The famous so-called "new car" smell is due to the migration and/or volatilization of various polymer stabilizing additives and plasticizers from the polymeric formulations widely employed in the manufacture of automobiles.

STATEMENT OF THE INVENTION

Thus it is desirable to have stabilizer compounds that function to stabilize polymers that are chemically bound to the polymer or polymer alloy being stabilized, thereby eliminating the problems that occur due to lack of solubility, migration, or volatility. Applicant has discovered a method of chemically incorporating into the polycarbonate polymer or polycarbonate copolymer molecule, compounds effective for stabilizing polycarbonate against the degradative and deleterious effects of ultraviolet radiation, the stabilizing properties of which are not affected by chemical incorporation into the polymers.

The present invention thus provides for a high molecular weight compound useful for stabilizing polymers against the effects of ultraviolet radiation generally comprising: (a) a condensation product comprising both (i) a bis-phenol derivative and (ii) a phosgene derivative or a carbonate ester, and (b) 3-(2H-benzotriazol-2-yl)-5-(1,1-dimethylethyl)-4-hydroxy-benzene-propanoic acid or structural variant thereof as an end capping agent for said condensation product wherein said end capping agent is chemically bound to said condensation product by an ester linkage and wherein the molecular weight of said high molecular weight compound is at least 1,125; the exception being the di-ester of a bis phenol compound with 3-(2H-benzotriazol-2-yl)-5-(1,1-dimethylethyl)-4-hydroxy-benzene-propanoic acid will also act as a stabilizer and when the bis phenol is bis phenol A the molecular weight is 871. Such a di-ester compound may be generally described as a compound of the formula:

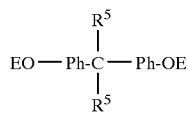

where each $R^5$ is independently selected from the group consisting of hydrogen, alkyl groups of from one to about nine carbon atoms, and aryl groups of from six to about fifteen carbon atoms, and E is an esterified acid selected from the group of acids having the formula:

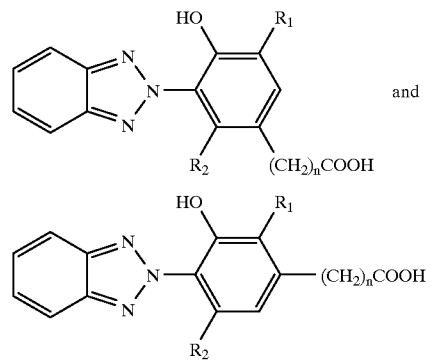

where $R_1$ is selected from the group of two to twelve carbon atom alkyl groups, preferably branched alkyl groups containing four to twelve carbon atoms, $R_2$ is selected from the group of hydrogen or one to twelve carbon atom alkyl groups and n varies from 0 to 20; wherein the molecular weight is at least 871. The present invention further provides for such a high molecular weight compound wherein said condensation product comprising both a bis phenol derivative and a phosgene derivative is a polymer. The present invention also provides for a stabilized polymer comprising polycarbonate resistant to the effects of ultraviolet radiation comprising said high molecular weight compound.

Additionally the present invention provides for a variety of methods to manufacture the high molecular weight stabilizing compound of the present invention:

1) a first process for the preparation of said high molecular weight stabilizer compound comprising the interfacial condensation of a phosgene derivative and a bis-phenol derivative to produce a condensation product wherein (a) while the phosgene derivative and the bisphenol derivative are reacted in the presence of 3-(2H-benzotriazol-2-yl)-5-(1,1-dimethylethyl)-4-hydroxy-benzene-propanoic acid and a suitable catalyst, (b) a base is subsequently added;

2) a second process for the preparation of said high molecular weight stabilizing compound comprising the melt trans-esterification of a carbonate ester and a bis-phenol derivative wherein (a) a carbonate ester and a bisphenol derivative are mixed together along with 3-(2H-benzotriazol-2-yl)-5-(1,1-dimethylethyl)-4-hydroxy-benzene-propanoic acid and a suitable catalyst and, (b) heating the blend under conditions of reduced pressure whereby condensation polymerization occurs;

3) a third process for the preparation of said high molecular weight stabilizing compound comprising (a) melting a polymer comprising polycarbonate, and (b) adding thereto 3-(2H-benzotriazol-2-yl)-5-(1,1-dimethylethyl)-4-hydroxy-benzene-propanoic acid; and 4) a fourth process for the preparation of said high molecular weight stabilizer compound comprising (a) mixing a polymer comprising polycarbonate and 3-(2H-benzotriazol-2-yl)-5-(1,1-dimethylethyl)-4-hydroxy-benzene-propanoic acid, (b) feeding the mixture to an extruder, and (c) processing the mixture under conditions of melt processing at a temperature sufficient to effect reaction. It is to be understood that when the compound 3-(2H-benzotriazol-2-yl)-5-(1,1-dimethylethyl)-4-hydroxy-benzene-propanoic acid is referred to herein, structural variants as hereinafter described and as described in U.S. Pat. Nos. 4,853,471; 4,973,702; and 5,032,498 may be substituted to achieve the same purpose.

The present invention further provides for articles of manufacture comprising the high molecular weight stabilizer compound of the present invention. Such articles of manufacture may exist in a variety of forms such as sheet, film, molded articles, and the like. Particularly useful applications for the compound of the present invention would include, but are not limited to, articles such as glazing materials, automobile headlight and taillight lenses, eyeglass lenses, and other uses where the both the physical optical properties of the materials comprising the compound of the present invention would render such use advantageous. Other particularly useful applications for the compounds of the present invention include articles such as sheet manufactured by coextrusion or molded articles manufactured by an insert injection molding process whereby the high molecular weight stabilizing compound of the present invention is present as a protective layer or as a protective surface layer, with the remainder of the article being a resin or mixture of resins, preferably polycarbonate or copolymers thereof that would benefit from such layering or protective layering.

Thus, the present invention overcomes the problems associated with decreases in stabilizer concentration due to the poor miscibility, poor dispersibility or high volatility of the low molecular weight stabilizer molecules, by comparison to the high molecular weight polymer molecule, by converting a monomeric stabilizer molecule into a functionalized polymeric molecule, simultaneously preserving the stabilizing function, lowering the volatility, and improving the miscibility or dispersibility of the stabilizing polymer molecule. This reduces losses of expensive stabilizer compounds during processing of polymers, and reduces downtime during manufacturing. The polymers so created may be used as stabilizers in polymers, polymer alloys or formulated into products directly.

DETAILED DESCRIPTION OF THE INVENTION

There is provided by the present invention, a chain stopper selected from the group of compounds having the formula:

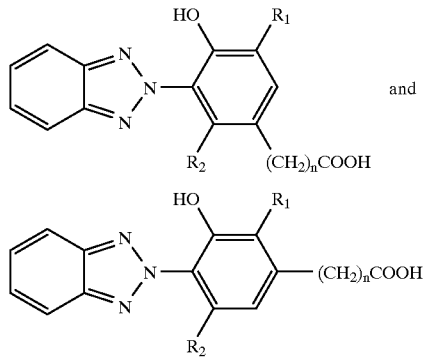

where $R_1$ is selected from the group of two to twelve carbon atom alkyl groups, preferably branched alkyl groups containing four to twelve carbon atoms, and $R_2$ is selected from the group of hydrogen or one to twelve carbon atom alkyl groups and where n ranges from zero to about twelve, useful for terminating or chain stopping polycarbonate comprising polymers.

There is provided by the present invention, a polycarbonate composition comprising a chain stopper selected from the group of compounds having the formula:

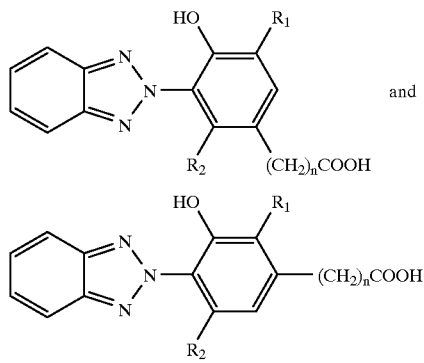

where $R_1$ is selected from the group of two to twelve carbon atom alkyl groups, preferably branched alkyl groups containing four to twelve carbon atoms, and $R_2$ is selected from the group of hydrogen or one to twelve carbon atom alkyl groups and where n ranges from zero to about twelve, and a bisphenol of the formula:

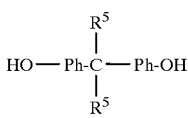

where each $R^5$ is independently selected from the group consisting of hydrogen, alkyl groups of from one to about nine carbon atoms, and aryl groups of from six to about fifteen carbon atoms, wherein the polycarbonate is useful for the various applications known for polycarbonate comprising polymers, and wherein the polycarbonate is useful as a stabilizer against the degradative effects of ultraviolet radiation for other polycarbonate comprising formulations.

There is provided by the present invention a method for making the polycarbonate composition of the present invention, comprising, (a) effecting reaction under interfacial reaction conditions at a pH in the range of about 7 to about 12 with a chain-stopper selected from the group of compounds having the formula:

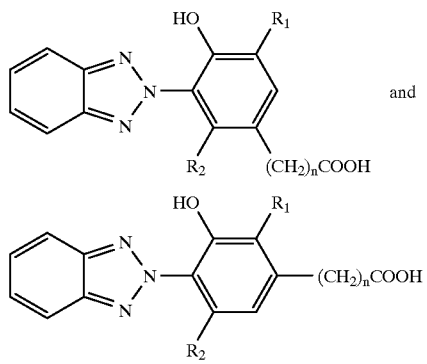

where $R_1$ is selected from the group of two to twelve carbon atom alkyl groups, preferably branched alkyl groups containing four to twelve carbon atoms, and $R_2$ is selected from the group of hydrogen or one to twelve carbon atom alkyl groups and where n ranges from zero to about twelve, and a bisphenol of the formula:

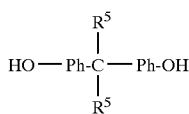

where each $R^5$ is independently selected from the group consisting of hydrogen, alkyl groups of from one to about nine carbon atoms, and aryl groups of from six to about fifteen carbon atoms, and a substantially stoichiometric amount of phosgene in the presence of an amount of a tertiary amine catalyst having the formula:

$R^6{}_3N$ and optionally a phase transfer catalyst, where each of the $R^6$ are independently selected from the group of $C_2$ to $C_{10}$ alkyl radicals and which is effective for providing polycarbonate. The lowest molecular weight oligomeric molecule exemplary of the compounds of the present invention is a carbonate of bis-phenol A comprising one carbonate unit and two units of bis phenol A and two chain stopping molecules, 3-(2H-benzotriazol-2-yl)-5-(1,1-dimethylethyl)-4-hydroxy-benzenepropanoic acid condensed to form an ester linkage between the terminal phenol hydroxy group of the two bis phenol moieties and the carboxylic acid functionality of the chain stopper having a molecular weight of at least 1,125. The di-ester of bis phenol A with 3-(2H-benzotriazol-2-yl)-5-(1,1-dimethylethyl)-4-hydroxy-benzene-propanoic acid is also a stabilizing molecule of the present invention, having a molecular weight of 871.

Some of the bisphenols which are included within the herein above disclosed formula for bisphenol are, for example:

2,2-bis(4-hydroxy phenyl)propane (bisphenol A)
2,2-bis(4-hydroxy phenyl)butane (bisphenol B)
4,4-bis(4-hydroxy phenyl)heptane
2,2-bis(4-hydroxy phenyl)hexane
2,2-bis(4-hydroxy phenyl)pentane
2,2-bis(4-hydroxy phenyl)-4-methyl pentane
2,2-bis(4-hydroxy phenyl)heptane, and
3,3-bis(4-hydroxy phenyl)2,4-dimethyl pentane.

Some of the phase transfer catalysts which are included within formula (1) are for example:
$[CH_3(CH_2)_3]_4NX$
$[CH_3(CH_2)_5]_4NX$
$[CH_3(CH_2)_6]_4NX$, and
$CH_3[CH_3(CH_2)_3]_3NX$
where X is selected from Cl—, Br— or —$OR^4$, where $R^4$ is selected from the group consisting of alkyl radicals having from one to nine carbon atoms.

In addition to the phase transfer catalysts of the previously disclosed formula, there are also included phase transfer catalysts having the formulas,
$CH_3(C_4H_9)_3NX$,
$CH_3(C_4H_9)_3PX'$
$C_2H_5(C_6H_{13})_3NX$,
$(C_4H_9)_3N—(CH_2)_6—N(C_4H_9)_32X$,
$(C_3H_7)_3N—(CH_2)_6—N(C_3H_7)_32X$, and
$CH_3(C_5H_{11})_2N—(CH_2)_4—N(C_5H_{11})_2CH_32X$
where X is as previously defined.

In the practice of one form of the present invention, a mixture of bisphenol and a chain-stopper of the invention is phosgenated under interfacial reaction conditions in the presence of an organic solvent, in the presence of an effective amount of a polymerizing catalyst. While not wishing to be bound by any particular theory, it is believed that the chain stopper reacts with the growing live end of the polymer to form an ester linkage through the acid substituent of the phenolic substituent of the substituted benzotriazole. Since this mode of reaction leaves the phenolic hydroxyl group free to dissociate or hydrogen bond the stabilizing properties of the stabilizing chain stopper molecule remain undisturbed by this particular chemical reaction. Generally the quantity of catalyst used ranges from about 0.05 mole % to about 10.00 mole % catalyst based on the total moles of bisphenol and chain stopper present in the reaction medium; such quantity constituting an effective amount. The quantity of tertiary amine when used as a catalyst ranges from about 0.01 to 6.00 mole % based on the moles of bis-phenol-A present in the reaction medium, a more preferred range is 0.01 to 4.00 mole %, and the most preferred range is 0.20 to 2.50 mole %. Suitable organic solvents which can be used are, for example, chlorinated aliphatic hydrocarbons, such as methylene chloride, chloroform, carbon tetrachloride, dichloroethane, trichloroethane, tetrachloroethane, dichloropropane and 1,2-dichloroethylene; substituted aromatic hydrocarbons such as, chlorobenzene, o-dichlorobenzene, and the various chlorotoluenes. The chlorinated aliphatic hydrocarbons, especially methylene chloride, are preferred.

Sufficient alkali metal hydroxide can be utilized to raise the pH of the bisphenol reaction mixture to 10.5 prior to phosgenation to provide dissolution of some of the bisphenol and chain-stopper into the aqueous phase.

Aqueous alkali, or alkaline earth metal hydroxide can be used to maintain the pH of the phosgenation mixture which can be in the range of between about 7 to about 12 and preferably 8 to 11. Various methods of controlling pH exist during the reaction, a specifically preferred technique is taught in U.S. Pat. No. 5,025,081 herein incorporated by reference. Some of the alkali metal or alkaline earth metal hydroxides, which can be employed are for example, sodium hydroxide, potassium hydroxide, and calcium hydroxide. Sodium and potassium hydroxides and particularly sodium hydroxide is preferred.

Phosgenation of the bisphenol can be conducted in a wide variety of either batch or continuous reactors. Such reactors are, for example, stirred tank reactors, which may be either batch or continuous flow. Additional reactors which are included are agitated column and recirculating loop continuous reactors.

The volume ratio of aqueous to organic phase during and at the termination of the phosgenation reaction can be in the range of 0.2–1.1. Reaction temperature can be in the range of between about 15–50° C. When the preferred organic liquid is utilized, such as methylene chloride, the reaction may be conducted at reflux which can be 35°–42° C. The reaction can be conducted at atmospheric pressures, although sub- or superatmospheric pressures may be employed if desired.

During phosgenation, the mixture is agitated, such as, by using a stirrer or other conventional equipment. The phosgenation rate can vary from between about 0.02–0.2 mole of phosgene, per mole of bisphenol per minute.

Prior to polycarbonate recovery which can be achieved by standard techniques, such as filtration, decantation, and centrifugation, chloroformate end groups are normally substantially eliminated. The reaction mixture sometimes must be agitated for a long period of time until the presence of chloroformates can no longer be detected. Alternatively, the addition of an equivalent level of a phenolic compound, based on the level of chloroformate, can be added at the end of the reaction.

Depending upon the molecular weight of polycarbonate desired, chain-stoppers can be used in a proportion of from 0.05 to 8 mole % based on the total moles of bisphenol and chain-stopper. The composition of the present invention utilizes as a chain stopper the compound, 3-(2H-benzotriazol-2-yl)-5-(1,1-dimethylethyl)-4-hydroxy-benzenepropanoic acid, or homologs thereof as previously defined by the general formula herein before recited, non limiting examples are: 3-(2H-benzotriazol-2-yl)-5-(1,1-dimethylethyl)-4-hydroxy-benzene-ethanoic acid, 3-(2H-benzotriazol-2-yl)-5-(1,1-dimethylethyl)-4-hydroxy-benzene-methanoic acid, 3-(2H-benzotriazol-2-yl)-5-(1,1-dimethylethyl)-4-hydroxy-benzenebutanoic acid, 3-(2H-benzotriazol-2-yl)-5-(1,1-dimethylethyl)-4-hydroxy-benzene-pentanoic acid, 3-(2H-benzotriazol-2-yl)-5-(1,1-dimethylethyl)-4-hydroxy-benzene-isobutanoic acid, and the like. The quantity of chain stopper present in the synthesized polymer ranges from about 0.07 up to about 14 weight percent, more preferably from about 1 to about 12 weight percent and most preferably from about 2 to about 10 weight percent based on the composition of the finished polymer. The percentage of chain stopper present in polymer alloys comprising the high molecular weight stabilizer will vary according to the amount of chain stopper present in the high molecular weight polymeric stabilizer as synthesized and the quantity of other polymers alloyed therewith.

The forgoing describes the preparation of polycarbonate comprising polymers wherein the stabilizing molecule functioning as a chainstopper is directly incorporated into the termini of the polymer molecule as the polymer is being synthesized. Mixtures of chain stoppers may be employed to vary the mole ratio of stabilizing chain stopping molecules to those which have other functions or which merely function as chain stopping agents solely. Alternative methods of incorporating chain stopping agents may be employed such as trans-esterification. Under conditions of trans-esterification, the polymer is prepared at a higher average molecular weight than would be utilized in the final product. The polymer is then admixed with a suitable quantity of one or more chain stopping stabilizer compound(s) or mixture thereof followed by the optional addition of one or more trans-esterification catalysts and trans-esterified. The quantity of stabilizing chain stopping compound is calculated based on the desired final average molecular weight of the polymer. This process serves to incorporate the stabilizing chain stopping compound while reducing the molecular weight of the polymer. This process may be accomplished in a reaction vessel, with or without the catalyst, or as is demonstrated in the experimental section, it may accomplished under conditions of melt extrusion in an extruder.

One particular approach to transesterification is the reaction of carboxylic acid functional groups with polycarbonate resin. In U.S. Pat. Nos. 5,081,205; 4,960,839; 4,826,928; and 4,999,408; a carboxylic acid functional group attached as a side group or as a pendant group reacts via transesterification forming a cross link with another polymer chain. In U.S. Pat. No. 4,814,395, a carboxylic acid functional group attached as an end group on a polycarbonate chain reacts by this transesterification to yield a polycarbonate chain with hydroxyl end groups. In U.S. Pat. No. 4,762,896, an additive compound that is carboxylic acid functional such as stearic acid will react with a polycarbonate polymer to reduce the molecular weight of the polymer. In these examples, it is hypothesized that a carboxylic acid group reacts with a carbonate group in the polycarbonate resin, thereby generating two new polymer end groups and simultaneously reducing polymer molecular weight by cutting the polymer chain into two smaller polymer molecules. The reaction as hypothesized, proceeds according to the following path:

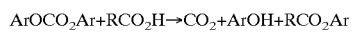

$$ArOCO_2Ar + RCO_2H \rightarrow CO_2 + ArOH + RCO_2Ar$$

generating a new ester linkage, a phenolic hydroxy end group, with the evolution of carbon dioxide. In the above reaction sequence, R is an alkyl or aryl group and Ar stands for a segment of a polycarbonate polymer.

An alternative approach to transesterification is the reaction of a carboxylate or carbonate ester functional group with a polycarbonate resin, utilizing an appropriate catalyst. The reaction is hypothesized to proceed along the following path:

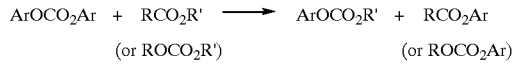

$$ArOCO_2Ar + RCO_2R' \longrightarrow ArOCO_2R' + RCO_2Ar$$
$$(\text{or } ROCO_2R') \qquad\qquad (\text{or } ROCO_2Ar)$$

where Ar and R are as defined before and R' is a different alkyl or aryl group.

Transesterification of polycarbonate polymers leads to at least three outcomes regarding measurable characteristics of the polymers, which outcomes are useful in measuring the extent to which the transesterification reaction has proceeded. First, when additional end groups are incorporated into the polymer the average molecular weight has been reduced. Second, incorporation of the carboxylic acid or ester into the polymer can be detected by analysis of the reacted polymer. Third, the amount of the unreacted or residual material may be analyzed. When the stabilizing end capping or chain stopping molecule has been incorporated into the polymer it may be detected by chemical or physical means; such incorporation at very low levels may be only slightly greater than zero. By the phrase, greater than zero, Applicant defines greater than zero as present in the polymer in a chemically or physically measurable amount using techniques known in the art.

Trans-esterification of polyester or polycarbonate type polymers, i.e. polycarbonate comprising polymers or copolymers and/or polyester or copolyester polymers, such as disclosed in the teachings of the instant invention, may lead to two outcomes. Two polymers may be melted together in the presence of a suitable catalyst and if there are present different chain stopping groups terminating the two polymers, trans-esterification and ester group exchange may be detected in the product. Alternatively, a given polymer may be melted in the presence of additional quantities of chain stopping agent either with or without a trans-esterification catalyst and the chain stopper will be incorporated into the polymer with a consequent reduction in molecular weight.

Polymer precursors to the stabilized and stabilizing polymers of the present invention may be made by a variety of techniques. Polycarbonates may be made by the techniques disclosed and taught in U.S. Pat. Nos. 3,030,331; 3,169,121; and 3,275,601 herewith incorporated by reference. Polyester polycarbonate copolymers may be made by the techniques disclosed and taught in U.S. Pat. Nos. 3,303,331; 4,194,038; 4,159,069; 4,188,314; and 4,923,933 herewith incorporated by reference. Polycarbonate siloxane copolymers may be made by the techniques disclosed in U.S. Pat. Nos. 3,419,634; 3,832,419; and 4,681,922. The polymer precursors are endcapped with an end stopping compound selected from the group of compounds having the formula:

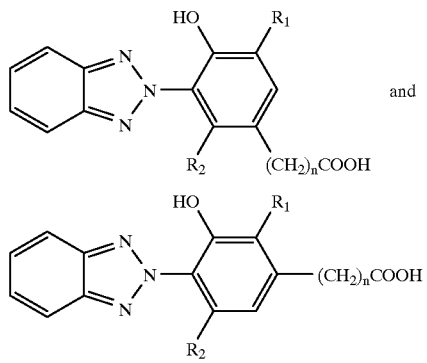

leading to the polymers of the present invention.

There is further provided by the present invention articles of manufacture comprising the stabilizing polymer of the present invention. A non-limiting example of such an article of manufacture would be an extruded sheet or film manufactured either wholly or in part from the stabilized polymer of the present invention.

All of the U.S. patents referenced herein are herewith specifically incorporated by reference.

EXPERIMENTAL

The following laboratory preparations indicate a reduction to practice of specific examples and embodiments of the present invention. On a laboratory scale, these examples are a demonstration of the best mode known to the inventor at the time of filing this application. Commercial scale embodiments of the various embodiments of this invention are believed to be achievable by the application of known techniques in the art of chemical reaction engineering and thus are intended to be covered by the claims appended hereto absent novel, unobvious, and unexpected difficulties or problems associated with scale-up from laboratory scale preparations to commercial scale preparations.

Analysis of resin samples for covalently bound 3-(2H-benzotriazol-2-yl)-5-(1,1-dimethylethyl)-4-hydroxy-benzenepropanoic acid residues was carried out by dissolving one gram of resin in 10 ml of methylene chloride, adding the methylene chloride solution of resin dropwise with stirring to 50 ml of acetone, then collecting and drying the precipitate. The level of covalently bound 3-(2H-benzotriazol-2-yl)-5-(1,1-dimethylethyl)-4-hydroxy-benzenepropanoic acid present was determined by UV adsorption at 343 nm wavelength using the assumption that the molar extinction coefficient of covalently bound 3-(2H-benzotriazol-2-yl)-5-(1,1-dimethylethyl)-4-hydroxy-benzenepropanoic acid was essentially identical to that for free 3-(2H-benzotriazol-2-yl)-5-(1,1-dimethylethyl)-4-hydroxy-benzenepropanoic acid.

Analysis of resin samples for 3-(2H-benzotriazol-2-yl)-5-(1,1-dimethylethyl)-4-hydroxy-benzenepropanoic acid was conducted by extraction of one gram of resin with 10 ml of acetonitrile, followed by a liquid chromatographic analysis with 70/30 acetonitrile/water to 100% acetonitrile over 15 minutes, then a 15 minute hold at 100% acetonitrile using a C-18 Bondapack column. Analysis of resin samples for molecular weight was conducted by gel permeation chromatographic analysis using a Waters Associates Model 150C instrument fitted with two ultrastyragel linear columns and one 500 angstrom ultrastyragel column, using chloroform as the solvent. The instrument was calibrated using bisphenol-A polycarbonate resin standards.

Example 1

Hydrolysis of 3-(2H-benzotriazol-2-yl)-5-(1,1-dimethylethyl)-4-hydroxy-benzenepropanoic acid, 1,6-hexandiyl ester (available commercially as Tinuvin 840® from Ciba-Geigy):

In a 1000 ml round bottom flask fitted with a heating mantel, magnetic stirrer, and a condenser capped with a drying tube were mixed 650 ml methanol and 56.0 g (1.0 mole) potassium hydroxide (KOH). After dissolution of the KOH, 190 g (0.25 mole) of 3-(2H-benzotriazol-2-yl)-5-(1,1-dimethylethyl)-4-hydroxy-benzenepropanoic acid, 1,6-hexandiyl ester was added. Upon heating to reflux, the reaction mixture turned to a clear dark red solution. Refluxing was continued for two days, with no visual change in the reaction mixture. The solids remained in solution upon cooling to room temperature. Acidification of the mixture with excess aqueous hydrochloric acid yielded a copious precipitate which was collected in a Buechner funnel, washed with a large excess of methanol and air dried. The material had a melting point of 190–195° C. Infrared analysis showed a typical carboxylic acid absorption peak at 1700 cm$^{-1}$. The melting point for Tinuvin 840® is 115–119° C. After recrystallization from ethyl acetate, the material had a melting point of 191–195° C. The compound prepared is 3-(2H-benzotriazol-2-yl)-5-(1,1-dimethylethyl)-4-hydroxybenzenepropanoic acid. Liquid chromatographic analysis indicated that the product as made contained approximately 11% methyl ester.

Example 2

Preparation of Polycarbonate endcapped with of 3-(2H-benzotriazol-2-yl)-5-(1,1-dimethylethyl)-4-hydroxybenzenepropanoic acid:

A 2000 ml four neck flask was fitted with a mechanical stirrer, a pH probe, a gas inlet tube, and a Claisen adapter fitted with a dry ice condenser and an aqueous caustic inlet tube. To the flask was added 325 ml of water, 400 ml of methylene chloride, 57 g (0.25 mole) bisphenol-A, 0.7 ml (0.005 mole, 2 mole %) triethyl amine, and 2.63 g (0.0077 mole, 3.1 mole %) of 3-(2H-benzotriazol-2-yl)-5-(1,1-dimethylethyl)-4-hydroxybenzenepropanoic acid, as prepared in example 1. Phosgene was introduced into the flask at a rate of 1 g/min. for thirty minutes holding the pH of the aqueous phase at a pH of 8 for the first 12 minutes of reaction and then holding the pH of the aqueous phase at a pH of 10.2 thereafter. At the end of the reaction the layers quickly separated. The resin solution had a slight yellow color. The methylene chloride layer was washed twice with a 2% aqueous solution of hydrochloric acid and three times with water, followed by drying over magnesium sulfate and precipitated with hot water in Waring blender. The powder resulting from the precipitate had a slight yellow color. Two additional batches were run in the same manner, with 3.48 g (4.1 mole %) and 3.9 g (4.6 mole %) of 3-(2H-benzotriazol-2-yl)-5-(1,1-dimethylethyl)-4-hydroxy-benzenepropanoic acid. Acidification of the brine layer from each of the reactions did not result in the formation of a precipitate. Results of analyses on the polycarbonates end-capped with 3-(2H-benzotriazol-2-yl)-5-(1,1-dimethylethyl)-4-hydroxy-benzenepropanoic acid are presented in

TABLE 1

Polycarbonate Endcapped with 3-(2H-benzotriazol-2-yl)-5-(1,1-dimethylethyl)-4-hydroxy-benzenepropanoic acid.

| Preparation | Mole % Endcapper | Weight % | MW | MN | Disp | $T_g$ ° C. |
|---|---|---|---|---|---|---|
| A | 3.1 | 4.2 | 35,100 | 11,500 | 3.07 | 151 |
| B | 4.1 | 5.6 | 28,200 | 9,800 | 2.88 | 149 |
| C | 4.6 | 6.2 | 24,300 | 8,400 | 2.88 | 147 |

The molecular weights of the three samples prepared are essentially identical to the molecular weights of the standard, commercial resins prepared with 3.1, 4.1, and 4.6 mole % conventional monofunctional end-capping agents (after making allowance for the fact that the carboxylic acid functional end-capping agent used herein contained approximately 11% of unreacted methyl ester). A liquid chromatographic analysis (LC) of the three resin samples in Table 1 indicated that less than 0.03 mole % of 3-(2H-benzotriazol-2-yl)-5-(1,1-dimethylethyl)-4-hydroxy-benzenepropanoic acid initially mixed with the polymer was present in an unreacted form. This strongly suggests complete incorporation of 3-(2H-benzotriazol-2-yl)-5-(1,1-dimethylethyl)-4-hydroxy-benzenepropanoic acid in the resin. An analysis of sample A (Table 1) for covalently bound 3-(2H-benzotriazol-2-yl)-5-(1,1-dimethylethyl)-4-hydroxy-benzenepropanoic acid showed 4.6 weight percent present in the re precipitated resin, confirming essentially complete incorporation. The variations between expected and theoretical are attributed to analytical precision and the possibility of some selective precipitation of the polymer bearing the 3-(2H-benzotriazol-2-yl)-5-(1,1-dimethylethyl)-4-hydroxy-benzenepropanoic acid functionality.

Based on the known reactivity of carboxylic acids under these reaction conditions (i.e. mono carboxylic acids incorporated as end caps as in U.S. Pat. No. 4,431,793 or dicarboxylic acids incorporated as co-monomers as in U.S. Pat. No. 5,025,081) and the molecular weight data indicating that 3-(2H-benzotriazol-2-yl)-5-(1,1-dimethylethyl)-4-hydroxy-benzenepropanoic acid incorporated as a monofunctional reagent, i.e. as an end-capping; the results obtained show that the highly hindered phenolic group in 3-(2H-benzotriazol-2-yl)-5-(1,1-dimethylethyl)-4-hydroxy-benzenepropanoic acid did not react under the reaction conditions employed. This conclusion is based on the assumption that if the phenolic hydroxy group of 3-(2H-benzotriazol-2-yl)-5-(1,1-dimethylethyl)-4-hydroxy-benzenepropanoic acid had been reactive, the compound would have been incorporated as a co-monomer resulting in a resin having a very high molecular weight due to the absence of an effective end-capping reagent.

Example 3

Preparation of the bisphenol-A di-ester of 3-(2H-benzotriazol-2-yl)-5-(1,1-dimethylethyl)-4-hydroxy-benzenepropanoic acid (2,2-bis(4-hydroxophenyl)propyl-bis-(3-(2H-benzotriazol-2-yl)-5-(1,1-dimethylethyl)-4-hydroxy-benzenepropanoate):

In a round bottom flask fitted with a condenser capped with a drying tube were mixed 33.9 g (0.1 mole) of 3-(2H-benzotriazol-2-yl)-5-(1,1-dimethylethyl)-4-hydroxy-benzenepropanoic acid, 30 ml of dry toluene, and 12 ml (0.156 mole) thionyl chloride. After 30 minutes of stirring at room temperature with no evidence of reaction, the flask was warmed to slightly below the reflux temperature which resulted in the evolution of gaseous hydrogen chloride. After four hours of reaction time, a sample was taken and subjected to analysis by infrared spectrophotometry, which indicated by virtue of a strong infrared absorption peak at 1796 cm$^{-1}$ that reaction was complete. After five and one half hours, the heat being supplied to the reaction was discontinued and the reaction mixture was allowed to stand three days. 75 ml of dry toluene was added to the reaction mixture and 50 ml of toluene was distilled away from the reaction mixture by a vacuum distillation, where the vacuum was created by aspiration, to remove excess thionyl chloride. The flask was cooled. To the contents of the cooled flask, 11.4 g bisphenol-A (0.05 mole) and 17.5 ml triethyl amine dissolved in 50 ml dry toluene were added. After reacting for two hours, crystals formed which were collected on a Buechner funnel. Removal of the solvent from the mother liquor yielded an oil which eventually crystallized. The two crystalline samples were washed with methanol and determined to be identical by comparison of their respective infrared absorption spectra. The combined weight of crystals recovered was 33.9 g. The crystalline material was recrystallized from toluene to yield 21 g of a slightly yellow crystalline solid which had a proton nmr spectrum in agreement with the structure of 2,2-bis(4-hydroxophenyl)propyl-bis-(3-(2H-benzotriazol-2-yl)-5-(1,1-dimethylethyl)-4-hydroxy-benzenepropanoate). Liquid chromatographic analysis indicated that the product as made contained approximately 4% unknown material.

Example 4

Melt Trans-esterification of Polycarbonate Resin to Incorporate a Stabilizing Chain Stopper.

Melt trans-esterification may be accomplished by any of several techniques known in the art. A particularly useful means of trans-esterifying the polymers of the present invention is to utilize a heated extruder as the reaction vessel in a so-called reactive extrusion. A quantity of 3-(2H-benzotriazol-2-yl)-5-(1,1-dimethylethyl)-4-hydroxy-benzenepropanoic acid sufficient to produce a 2 mole % level was blended into 450 g of a polycarbonate having a molecular weight of 33,000. Using a ¾" Wayne extruder, the mixture of polycarbonate and 3-(2H-benzotriazol-2-yl)-5-(1,1-dimethylethyl)-4-hydroxy-benzenepropanoic acid was extruded at 600° F. Incorporation of 2 mole % should generate approximately 4 mole % new end groups with the result that molecular weight of the polymer would be reduced, Table 2.

TABLE 2

Reactive Extrusion of Polycarbonate with Stabilizing End Capping Agent (3-(2H-benzotriazol-2-yl)-5-(1,1-dimethylethyl)-4-hydroxy-benzenepropanoic acid).

| Resin | Mole % End Capping | Mole % Stabilizing End Capper | Mol. Wt. (MW) | Mol. Wt. (MN) |
|---|---|---|---|---|
| Reference Resin #1 | 2.4 | 0 | 33,000 | 17,400 |
| Example 4A | 2.4 | 2.0 | 18,500 | 7,600 |
| Example 4B | 2.4 | 2.0 | 17,400 | 7,000 |
| Resin #2 | 6.5 | 0 | 16,700 | 7,700 |

Notes:
4A Sample taken at the beginning of the extrusion.
4B Sample taken at the end of the extrusion.

Melt transesterification, conducted as a reactive extrusion, reduced the molecular weight of the reference resin #1 from about 33,000 to about 18,000. For comparative purposes, molecular weight data on a standard, commercial reference resin, resin #2, prepared by the conventional means using 6.5 mole % end-capping agent (4.1 mole % more end-capping resin than reference resin #1) is given in Table 2. Inspection of the data shows that the two transesterified resin samples, 4A and 4B, are very close in molecular weight to the reference resin #2. This indicates that those two resins possess approximately 6.5% mole end groups. Consequently, transesterification generated an additional 4 mole % end groups in the reference resin #1, as would be predicted based on compete reaction of the 2 mole % acid supplied in the transesterification.

Example 5

Melt Transesterification of Polycarbonate Resin to Incorporate a Stabilizing Chain Stopper (larger scale example at a lower processing temperature)

A quantity of 3-(2H-benzotriazol-2-yl)-5-(1,1-dimethylethyl)- 4-hydroxy-benzenepropanoic acid sufficient to produce a 3.6 mole % level (4.6 weight %) was blended into 1800 g of a polycarbonate resin having a molecular weight of 33,000. The 3-(2H-benzotriazol-2-yl)-5-(1,1-dimethylethyl)-4-hydroxy-benzenepropanoic acid was prepared as in Example 1 with the addition of a final recrystallization using ethyl acetate. Minor amounts of epoxy and phosphite stabilizers as well as an optical brightener were blended in. The blend was extruded into pellets on a Werner-Pfleiderer SK30 twin screw extruder with temperature zones set at 465° F. to 480° F. The pellet sample was directly analyzed for polymer bound 3-(2H-benzotriazol-2-yl)-5-(1,1-dimethylethyl)-4-hydroxy-benzenepropanoic acid by re precipitation and UV analysis. Residual unreacted 3-(2H-benzotriazol-2-yl)-5-(1,1-dimethylethyl)-4-hydroxy-benzenepropanoic acid was analyzed for by LC. The results are set forth in Table 3.

TABLE 3

Reactive Extrusion of Polycarbonate with Stabilizer End Capping Agent 3-(2H-benzotriazol-2-yl)-5-(1,1-dimethylethyl)-4-hydroxy-benzenepropanoic acid (BzTrzl) (lower temperature extrusion with a second melt processing step)

| Formulated Levels | | Melt Processing | Molecular Weight | Analysis for BzTrzl | |
|---|---|---|---|---|---|
| Mole % | Wt.% | | | Wt. % Bound | Wt. % Free |
| 3.6 | 4.6 | single ext. 465–480° F. | 15,800 | 1.4 | 2.8 |
| 3.6 | 4.6 | single plus add'l. 1.5 min. at 500° F. | 10,700 | — | 0.5 |
| 3.6 | 4.6 | single plus add'l. 2 min. at 500° F. | 9,900 | — | 0.38 |
| 3.6 | 4.6 | single plus add'l. 3 min, at 500° F. | 9,500 | — | 0.13 |

Notes: All samples received are 465–480° F. twin screw extrusion with additional 500° F. second processing steps as indicated. The reported molecular weights are weight average molecular weight.

The results shown in table 3 indicate that a single reactive extrusion at 465–480° F. does not result in complete reaction of the 3-(2H-benzotriazol-2-yl)-5-(1,1-dimethylethyl)-4-hydroxy-benzenepropanoic acid. Of the initial 4.6 wt. % in the formulation, 1.4 wt. % is accounted for as a bound end-capping agent and the remaining 2.8 wt. % found as unreacted residue. The variance between 4.2 and 4.6 wt. % is attributed to uncertainties in analytical precision and accuracy since other reaction products of the 3-(2H-benzotriazol-2-yl)-5-(1,1-dimethylethyl)-4-hydroxy-benzenepropanoic acid were not analyzed for. This is conceivably the case in short chain oligomers containing bound 3-(2H-benzotriazol-2-yl)-5-(1,1-dimethylethyl)-4-hydroxy-benzenepropanoic acid that failed to re-precipitate. Repetition of the foregoing experiment with 3-(2H-benzotriazol-2-yl)-5-(1,1-dimethylethyl)-4-hydroxy-benzenepropanoic acid that had not been recrystallized from ethylacetate resulted in a sample having 1.7 wt. % free 3-(2H-benzotriazol-2-yl)-5-(1,1-dimethylethyl)-4-hydroxy-benzenepropanoic acid after the first extrusion. Repetition of this experiment with higher viscosity polycarbonate (higher molecular weight) resin essentially duplicated the results.

Example 6

Melt Trans-esterification of Polycarbonate Resin to Incorporate a Stabilizing Chain Stopper (repeat melt processing, with optional additional catalysts).

Samples of pellets prepared in Example 5 were dried at 115° C. for 2 hours, then starve fed into a small-scale bench top extruder (CSI MAX mixing extruder manufactured by Custom Scientific Corp.) set at 500° F. (260° C.) and 60 rpm. The minimum residence time for resin being processed by the extruder was approximately one minute. Longer residence times were obtainable by temporarily plugging the outlet of the extruder. Catalytic materials, e.g. acids and bases, were added to the pellet samples by dispersing quantities of the catalytic material onto samples of the polycarbonate resin producing a resin catalyst concentrate such that when 1 wt. % of the resin catalyst concentrate was added to the pellets from Example 5 the levels of catalyst listed in Table 4 were obtained.

The results of Table 3 demonstrate clearly that incremental additions of melt reaction processing in an extruder increase the approach to completion of the reaction between the polycarbonate polymer and the 3-(2H-benzotriazol-2-yl)-5-(1,1-dimethylethyl)-4-hydroxy-benzenepropanoic acid end capping reagent. The results in Table 4 show that a basic catalyst accelerated melt transesterification and that a mildly acidic catalyst was not particularly effective at promoting a faster melt transesterification. This result might be explainable on the basis that extremely low levels of base (parts per billion or low parts per million) are carried over into the resin product and act to catalyze transesterification. More aggressively acidic and basic materials are known to catalyze transesterification.

TABLE 4

Reactive Extrusion of Polycarbonate with Stabilizing
End Capping Agent, 3-(2H-benzotriazol-2-yl)-5-
(1,1-dimethylethyl)-4-hydroxy-benzenepropanoic acid
(second melt processing step with added catalyst)

| Duration of Second Melt Processing (min.) | Catalyst | Molecular Weight | Weight Percent Free BzTrzl |
|---|---|---|---|
| 0 | none | 15,800 | 2.8 |
| 1.5 | none | 10,700 | 0.5 |
| 2.0 | none | 9,900 | 0.38 |
| 3.0 | none | 9,500 | 0.13 |
| 1.5 | 200 ppm acid | 13,900 | — |
| 2.0 | 200 ppm acid | 13,800 | — |
| 3.0 | 200 ppm acid | 14,800 | — |
| 1.0 | none | 9,900 | 0.081 |
| 1.5 | none | 9,300 | 0.0066 |
| 2.0 | none | 8,850 | NDA |
| 1.0 | 0.025 mole % base | 9,800 | 0.049 |
| 1.5 | 0.025 mole % base | 9,000 | 0.0051 |
| 2.0 | 0.025 mole % base | 9,200 | 0.0055 |

Notes to Table 4:
1. All samples were prepared such that the level of 3-(2H-benzotriazol-2-yl)-5-(1,1-dimethylethyl)-4-hydroxy-benzenepropanoic acid was 3.6 mole % (4.6 weight %).
2. All samples received a first melt processing step at 465–480° F. as well as the second melt processing described in the Table.
3. The acid catalyst used was 2:1 weight ratio blend of tris(nonylphenyl)phosphite to phosphorus acid.
4. The base catalyst used was tetraethylammonium hydroxide.
5. The two sets of samples reprocessed without catalyst were run in separate experiments and serve as controls respectively, for the acid and base experiments listed below them in the Table. For both, essentially complete reaction was observed after 2–3 minutes of reprocessing. The differences between them are attributable to the variation in reaction temperature and reaction time that typically occur when using small scale extrusion apparatus.

Having described the invention that which is claimed is:

1. A stabilized polymer comprising polycarbonate resistant to ultraviolet radiation comprising a high molecular weight compound comprising:

(a) a condensation product comprising
      (i) a bis-phenol derivative and
      (ii) a phosgene derivative or a carbonate ester, and (b) an endcapping or chain stopping molecule selected from the group consisting of a compound of the formula:

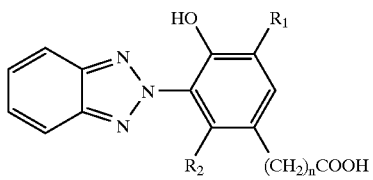

and a compound of the formula:

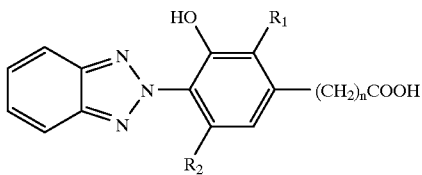

where $R_1$ is selected from the group of two to twelve carbon atom alkyl groups, $R_2$ is selected from the group of hydrogen or one to twelve carbon atom alkyl groups and n varies from 0 to 20; as an end capping agent for said condensation product wherein said end capping agent is chemically bound to said condensation product by an ester linkage and wherein the molecular weight of said high molecular weight compound is at least 1,125.

2. A stabilized polymer comprising polycarbonate resistant to ultraviolet radiation comprising the high molecular weight compound of claim 1.

3. The stabilized polymer of claim 2 wherein the high molecular weight compound is present in an amount wherein the quantity of chain stopping or endcapping compound chemically bound as an end capping agent via an ester linkage is present in the stabilized polymer ranging in an amount of from about 0.07 up to about 14.0 weight percent.

4. The high molecular weight compound of claim 3 wherein the phosgene derivative is a chloroformate compound.

5. An article of manufacture comprising the compound of claim 1.

6. The article of manufacture of claim 5 wherein said article of manufacture is a sheet.

7. The article of manufacture of claim 5 wherein said article of manufacture is a film.

8. The article of manufacture of claim 5 wherein said article of manufacture is a molded article.

9. A polymer stabilized against the effects of ultraviolet radiation comprising:

(a) a condensation product comprising both
      (i) a bis-phenol derivative and
      (ii) a phosgene derivative or a carbonate ester, and (b) a di-ester of the formula:

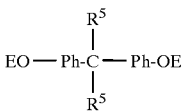

where each $R^5$ is independently selected from the group consisting of hydrogen, alkyl groups of from one to about nine carbon atoms, and aryl groups of from six to about fifteen carbon atoms, and E is an esterified acid selected from the group of acids having the formula:

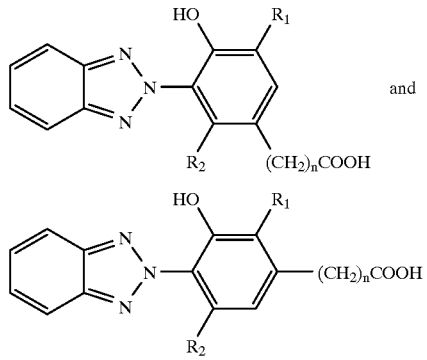

and where $R_1$ is selected from the group of two to twelve carbon atom alkyl groups, $R_2$ is selected from the group of hydrogen or one to twelve carbon atom alkyl groups and n varies from 0 to 20; wherein the ester linkages of said di-ester is formed from the carboxylate group of said acid and wherein the molecular weight is at least 871.

10. An article of manufacture comprising the polymer of claim 9.

* * * * *